(12) United States Patent
Bergner et al.

(10) Patent No.: US 9,901,319 B2
(45) Date of Patent: Feb. 27, 2018

(54) MINIMUM BACKGROUND ESTIMATION FOR PERIPHERAL EQUALIZATION

(71) Applicant: KONINKLIJKE PHILIPS N.V., Eindhoven (NL)

(72) Inventors: Frank Bergner, Hamburg (DE); Hanno Heyke Homann, Hannover (DE); André Goossen, Radbruch (DE); Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/326,053

(22) PCT Filed: Nov. 16, 2015

(86) PCT No.: PCT/EP2015/076662
§ 371 (c)(1),
(2) Date: Jan. 13, 2017

(87) PCT Pub. No.: WO2016/079042
PCT Pub. Date: May 26, 2016

(65) Prior Publication Data
US 2017/0265830 A1    Sep. 21, 2017

(30) Foreign Application Priority Data
Nov. 18, 2014 (EP) ..................... 14193577

(51) Int. Cl.
*G06K 9/00* (2006.01)
*A61B 6/00* (2006.01)
(Continued)

(52) U.S. Cl.
CPC ........... *A61B 6/5211* (2013.01); *A61B 6/502* (2013.01); *G06T 5/008* (2013.01); *G06T 7/0012* (2013.01);
(Continued)

(58) Field of Classification Search
None
See application file for complete search history.

(56) References Cited

U.S. PATENT DOCUMENTS 8,428,324 B2 * 4/2013 Heinlein ............... A61B 6/502
250/252.1
2007/0047793 A1    3/2007 Wu
(Continued)

FOREIGN PATENT DOCUMENTS

EP         2131325        12/2009

OTHER PUBLICATIONS

Bick, et al., "Density Correction of Peripheral Breast Tissue on Digital Mammograms", Radiographics, vol. 16, No. 6, 1996.
(Continued)

*Primary Examiner* — Vikkram Bali

(57) ABSTRACT

The invention relates to peripheral equalization during a mammography X-ray examination. High contrast tissue pixel values are removed from the background estimate by finding the minimum intensity values of the pixel located in the neighborhood, which have approximately the same distance to the skin line. Thus, high attenuating pixel values may be removed from the estimate and replaced by lower attenuating tissue pixel values. After a minimum filtration, a conventional peripheral equalization is performed. This may result in less overshoots and intensity values for higher attenuating structures in the peripheral region may become more consistent with intensity values for higher attenuating structures in the fully compressed region.

20 Claims, 2 Drawing Sheets

(51) Int. Cl.
*G06T 5/00* (2006.01)
*G06T 7/12* (2017.01)
*G06T 7/00* (2017.01)
*A61B 6/04* (2006.01)

(52) U.S. Cl.
CPC .............. *G06T 7/12* (2017.01); *A61B 6/0414* (2013.01); *G06T 2207/10116* (2013.01); *G06T 2207/30068* (2013.01)

(56) References Cited

U.S. PATENT DOCUMENTS

| | | | |
|---|---|---|---|
| 2009/0080752 A1* | 3/2009 | Ruth | G06K 9/4638 382/132 |
| 2010/0046814 A1 | 2/2010 | Dewaele | |
| 2011/0026791 A1* | 2/2011 | Collins | G06K 9/62 382/131 |

OTHER PUBLICATIONS

Tortajada, et al., "Breast peripheral area correction in digital mammograms", Computers in Biology and Medicine, vol. 50, Jul. 1, 2014.

Highnam, et al., "Estimation of compressed breast thickness during mammography", The British Journal of Radiology, 71 (1998), 646-653, 1998 The British Institute of Radiology.

Mawdsley, et al., "Accurate estimation of compressed breast thickness in mammography", Med. Phys. 26, Feb. 2009.

Hauge, et al., "The readout thickness versus the measured thickness for a range of screenfilm mammography and full-field digital mammography units", Med. Phys. 39, Jan. 2012.

Heine, et al., "Effective radiation attenuation calibration for breast density: compression thickness influences and correction", BioMedical Engineering OnLine 2010, 9:73.

J. Zoetelief, M. Fitzgerald, W. Leitz and M. Säbel. European protocol on dosimetry in mammography.EUR 16263, Luxemburg: EC, 1996.

R. van Engen, K. Young, H. Bosmans and M. Thijssen. Addendum on digital mammography to chapter 3 of the European guidelines for quality assurance in mammography screening, ver 1.0, 2003, EUREF.

Pisano, et al., "Image Processing Algorithms for Digital Mammography: A Pictorial Essay", RSNA 2000.

Snoeren, et al., "Thickness Correction of Mammographic Images by Means of a Global Parameter Model of the Compressed Breast", IEEE Transactions on Medical Imaging, vol. 23, No. 7, Jul. 2004.

Byng, et al., "Thickness-Equalization Processing for Mammographic Images", RSNA 1997.

Kallenberg, et al., "Compression paddle tilt correction in full-field digital mammograms", 2012 Institute of Physics and Engineering in Medicine.

* cited by examiner

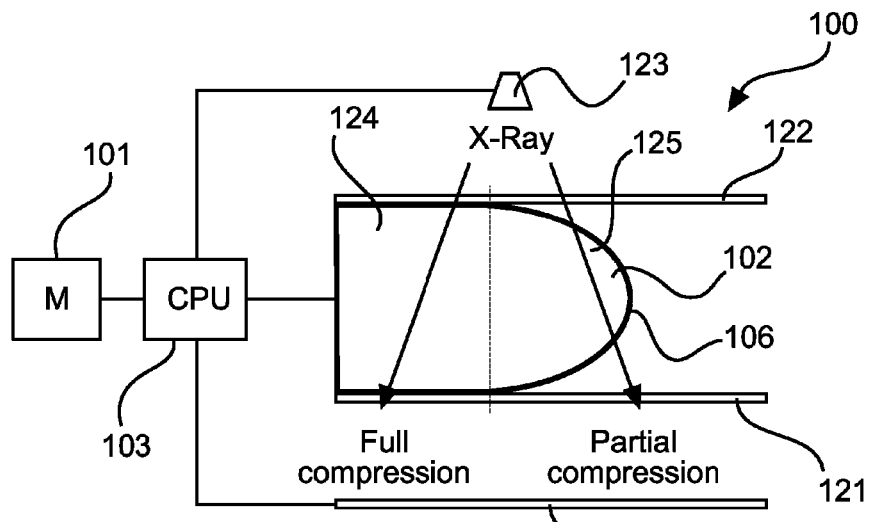
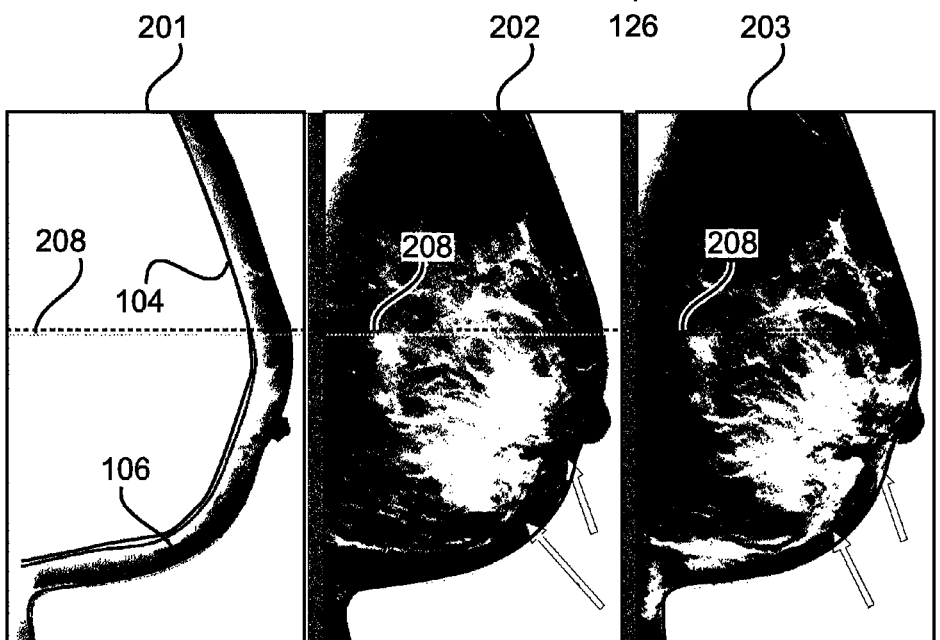
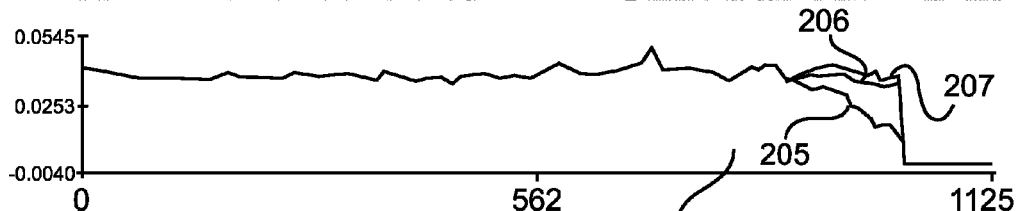
Fig. 2

MINIMUM BACKGROUND ESTIMATION FOR PERIPHERAL EQUALIZATION

CROSS REFERENCE TO RELATED APPLICATIONS

This application is the U.S. National Phase application under 35 U.S.C. § 371 of International Application No. PCT/EP2015/076662, filed Nov. 16, 2015, published as WO2016/079042 on May 26, 2016, which claims the benefit of European Patent Application Number 14193577.5 filed Nov. 18, 2014. These applications are hereby incorporated by reference herein.

FIELD OF THE INVENTION

The invention relates to the field of X-ray imaging. In particular, the invention relates to an examination apparatus for examination of an object of interest, a method of examination an object of interest, a computer-readable medium, and a program element.

BACKGROUND OF THE INVENTION

In x-ray imaging, an object of interest to be examined by an X-ray examination apparatus may have a non-constant thickness, in particular in its periphery, i.e. in its boundary area. In mammography and breast tomosynthesis, the patient's breast, i.e. the object of interest, can be compressed between two compression paddles and then scanned using an X-ray source. In the peripheral regions, where the breast does not touch the paddles any more, the X-ray attenuation of the X-rays may be less than in the central region of the object. In order to allow a single grey scale window for viewing, this effect may need to be compensated. For this purpose, so-called peripheral equalization methods may be used.

ULRICH BICK ET AL: "Density Correction of Peripheral Breast Tissue on Digital Mammograms", RADIOGRAPHICS, vol. 16, no. 6, 1 Nov. 1996, pages 1403-1411, describe an examination apparatus wherein digital mammograms are viewed on video displays. An algorithm has been developed for selective enhancement (i.e. density correction) of the dark peripheral portions of the female breast on mammograms.

SUMMARY OF THE INVENTION

It may be desirable to improve the image of an object of interest in the peripheral regions of the object.

Aspects of the invention are stated in the independent claims. Advantages and further embodiments are set out in the dependent claims, the description and the figures.

A first aspect of the invention relates to an examination apparatus for examination of an object of interest. The examination apparatus comprises a storage unit and a processing unit. The storage unit is designed to store and provide image data of an image of the object of interest, e.g. a female breast, to the processing unit. The image data comprises object data, which relates to the object of interest, and non-object data, which relates to areas outside the object of interest.

The processing unit is programmed to perform a segmentation of the object data from the non-object data and to determine a line, which is an iso-contour and extends at a constant distance from a boundary of the object of interest and/or extends in a region of constant thickness of the object of interest.

The processing unit is also programmed to generate a minimum filtered image of the object of interest by performing a minimum filtering of the object data along the iso-contour, thereby replacing a higher intensity value of a first pixel, positioned on the iso-contour, by a lower intensity value of a second pixel, which is positioned on the iso-contour in the neighborhood of the first pixel, for example adjacent to the first pixel or with a few (for example not more than 20 or 30) pixel between the first pixel and the second pixel. Thus, a new, minimum filtered image is created. The processing unit is also programmed to perform a peripheral equalization of the object data after generation of the minimum filtered image.

It may be seen as a gist of the invention that the peripheral equalization of the object data is enhanced by finding the attenuation minima along paths with equal distance to the skin line of the breast. This may help to reduce thickness overestimation around highly attenuating structures, and in the majority of cases this may help to reduce undershoot artifacts caused by conventional peripheral equalization.

The processing unit is adapted, i.e. programmed, for performing, during the peripheral equalization, a determination of a background data estimate by low-pass filtering the minimum-filtered image, subtracting the background data estimate from the image data and adding a desired homogeneous background attenuation image to the image data, from which the background data estimate has been subtracted.

According to an exemplary embodiment of the present invention, the processing unit is adapted for performing a pre-blurring of the object data before the minimum filtering, using a low-pass filter.

The iso-contour may be determined by an evaluation of spectral data acquired during the examination procedure. In spectral X-ray imaging, a detector may be used that is capable to discriminate the energies of incoming photons. One example of such a detector is a photon counting detector with at least two energy thresholds. The X-ray attenuation that takes place between the X-ray tube and the detector is mainly based on two major effects: the photoelectric effect and the Compton scatter. Thus, it may be possible to transform the measurements from the different energy-levels of the detector onto these two effects, i.e., the measured attenuation by photo effect and the Compton scatter.

In case of mammographic imaging, this transform may be, alternatively, calibrated to give an estimate for glandular and fatty tissue intersection lengths, as these tissues have different photo/Compton properties.

The process of mapping measured photon intensities or counts into an estimate for the intersection lengths through different materials is called material decomposition. This process may be either function based or look-up table based, and it may have to be calibrated upfront for each detector by inserting different known material compositions into the beam of a detector element. Thus, a mapping may be derived that converts a received detector reading from two or more energy bins into a calibrated material combination.

According to another exemplary embodiment of the invention, the iso-contour is determined by identifying the boundary of the object of interest from the non-object data, the object data and/or the image data. In case the object of interest is a breast, the boundary is the skin of the breast.

Thus, the iso-contour is determined in a geometrical manner by identifying the boundary of the object and by defining the iso-contour to be a line parallel to the boundary line, i.e., with a constant distance to the object of interest.

The examination apparatus may be adapted in such a way that the minimum filtering of the object data along the iso-contour comprises a selection of a first pixel, a determination of the intensity value of the first pixel, a determination of each intensity value of each of a predetermined number of neighboring pixel positioned on the iso-contour, which runs through the first pixel, and which are adjacent to the first pixel. In the image generated by the minimum filtering of the object data (i.e. the "minimum filtered image"), a replacement of the intensity value of the first pixel by the lowest intensity value of the predetermined number of adjacent pixel is performed, if a lower intensity value exists. If the intensity value of the first pixel is lower or equal to the lowest intensity value of the predetermined number of neighboring pixel, no replacement of the intensity values takes place. The original image, i.e. the original object data, may not be changed during this minimum filtering process, but a minimum filtered image is created.

After that, a corresponding minimum filtering is performed for the pixel next to the first pixel, which may result in an update of the image generated by the minimum filtering of the object data (if a neighboring pixel has a lower intensity value than the pixel next to the first pixel), and so on, until all pixel in the peripheral region of the object have been minimum-filtered and the minimum filtered image has been generated.

According to another exemplary embodiment of the present invention, the peripheral equalization of the object data comprises a low-pass filtering.

The examination apparatus may be adapted as a two-dimensional mammography examination apparatus or a tomosynthesis examination apparatus.

Another aspect of the invention relates to a method of examining an object of interest, in which image data of an image the object of interest is acquired, the image data comprising object data and non-object data. Then, a segmentation of the object data from the non-object data is performed and a line, which is an iso-contour and which extends at a constant distance from a boundary of the object of interest and/or which extends along a constant thickness of the object of interest, is determined.

A minimum filtering of the object data is performed along the iso-contour, thereby replacing a higher intensity value of a first pixel positioned on the iso-contour by a lower intensity value of a second pixel positioned on the iso-contour, which is positioned in the neighborhood of the first pixel, resulting in a minimum filtered image. Then, a peripheral equalization of the object data is performed.

Another aspect of the invention relates to a computer-readable medium comprising a program element, which, when being executed by a processing unit, is adapted to instruct the processing unit to carry out the method steps described above (and also further below).

According to another aspect of the present invention, a program element is provided, which, when being executed by a processing unit, is adapted to instruct the processing unit to carry out the above (and also further below) described method steps.

These and other aspects of the invention will be apparent from and elucidated with reference to the embodiments described hereinafter.

BRIEF DESCRIPTION OF THE DRAWINGS

FIG. 1 shows an examination apparatus according to an exemplary embodiment of the invention.

FIG. 2 shows three images of a breast.

DETAILED DESCRIPTION OF EMBODIMENTS

Figure 3:
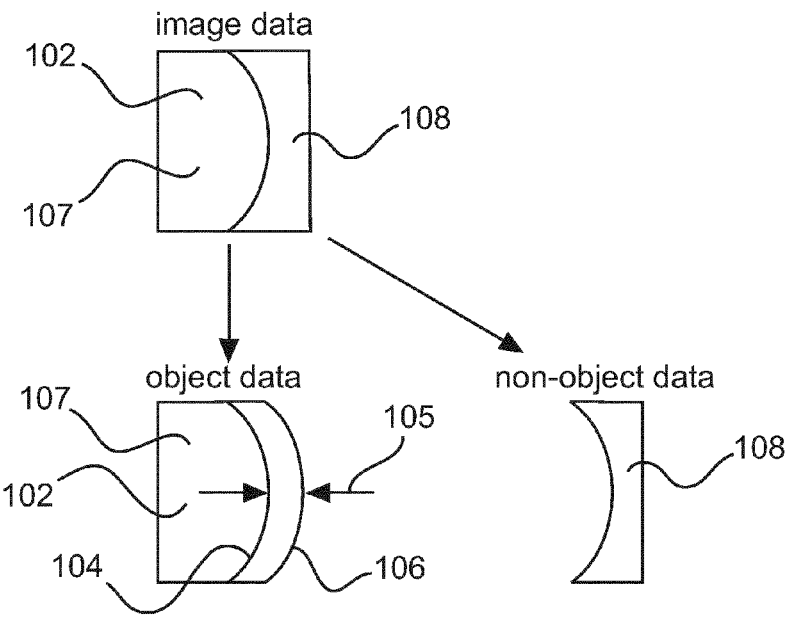
FIG. 3 shows method steps according to an exemplary embodiment of the invention.

The figures are schematic and not true to scale. If the same reference signs are used in different figures, they may refer to identical or similar elements. However, similar or identical elements may also be labeled with different reference signs.

FIG. 1 shows an examination apparatus 100 according to an exemplary embodiment of the invention. The examination apparatus may be adapted as a spectral X-ray examination apparatus, a mammography examination apparatus and/or a tomosynthesis examination apparatus.

The examination apparatus 100 comprises an X-ray source 123 from which X-rays can be emitted towards the object of interest 102, i.e., a female breast. The breast is positioned between two compression paddles or compression plates 121, 122. The more central region 124 of the breast is fully compressed and has a constant thickness, wherein the more peripheral region 125 of the breast is only partial compressed and has a thickness which decreases towards the peripheral edge 106, i.e. the boundary or skin line of the breast.

On the other side of the object of interest, a detector array 126 may be arranged which detects the radiation on the X-ray source which has passed the object of interest.

The examination apparatus 100 is controlled by a processing unit 103, which is connected to a storage unit 101, on which the image data acquired by the examination apparatus may be stored.

In mammography and breast tomosynthesis, the radiologist may have the desire to see all relevant image details using a single grey scale level and window. As the attenuation of the breast 102 is lower in the non-compressed regions 125, which extend towards the skin line 106, a so-called peripheral equalization may be performed to lift the outer attenuation levels up to the preferred mean breast attenuation, which fits the single level/window setting. The peripheral equalization may be performed by subtracting an estimated mean attenuation of the breast (background data estimate) in the individual regions and add back the desired background attenuation level, which is typically homogeneous. One way of obtaining the background data estimate is blurring the object data, i.e. the image of the breast, by means of low-pass filtering.

However, blurring the image means that tissue with higher attenuation will increase the estimated mean attenuation. Correcting the image with an overestimated value may cause undershoots, in particularly close to high contrast structures. This is shown in image 202 of FIG. 2 (see the two arrows). Reference numeral 201 denotes the original image without equalization.

The minimum filtering according to an exemplary embodiment of the invention is performed along the iso-contour 104, which is a curved line with constant distance to the skin line 106. In the ideal case only the fatty background tissue with less attenuation and not structures like glandular tissue, which may have a higher density but not necessary longer intersection lengths in the volume, is taken into account. Taking out these structures from the estimation may reduce the overestimation of the breast thickness and also the undershoots.

According to an exemplary embodiment of the invention, the blurring method for background estimation is extended by removing high contrast tissue pixel values from the object data, if possible.

This may be done by finding the minimum intensity pixel value among the pixels in the neighborhood of a first pixel, wherein all these pixel have approximately the same distance to the skin line and/or are positioned on a path along which the thickness of the breast is constant. This approach may remove high attenuating pixel values from the background data estimate and replace them with low attenuating tissue pixel values. In the ideal case, these are fatty tissue values, if such are present.

After the minimum filtering, a conventional peripheral equalization may be performed, which may now result in less overshoots, as can be seen from picture 203 in FIG. 2. Furthermore, intensity values for higher attenuating structures (such as glandular tissue) in the peripheral region may become more consistent with corresponding structures in the fully compressed region.

Diagram 204 shows the pixel intensity along intersection 208 for image 201 (see plot 205), image 202 (see plot 206) and image 203, which has been processed according to an exemplary embodiment of the present invention (see plot 207). As can be seen from diagram 204, plot 207 reflects more constant pixel values than the original image (plot 205) and image 202, which has been processed with conventional peripheral equalization without minimum filtering.

FIG. 3 shows the original image data of a breast 102, which comprises object data 107 and non-object data 108. In the separation step, the image data is separated into two data sets, one containing the object data and the other one containing the non-object data. An iso-contour 104 is then defined in the image generated from the object data, which iso-contour 104 has a constant distance 105 from the skin line 106 of the object of interest 102.

According to an aspect of the invention, a minimum filtration is performed along iso-contours of the breast, which are located in the peripheral region of the breast (where the breast is of non-constant thickness). The method is based on the idea that the thickness of the breast along those lines should be approximately equal. Additionally, the fatty, lowly attenuating tissue may be more suitable as a background estimate than highly attenuating glandular tissue, so it is preferred. The minimum filtration may only be performed in a local neighborhood of a selected, first pixel, so variations in the breast background do not need to be taken into account. If the minimum filtration only finds high attenuating tissue, then the filter output is at least not worse than in the conventional approach.

In case of spectral tomosynthesis, this approach may be refined in the following way: From the data acquired during the measurement estimates of how much glandular and fatty tissue has been intersected by the corresponding x-ray can be derived. For an accurate thickness equalization it may be necessary to reconstruct the fatty tissue amount at each part of the volume, which may not be possible due to the limited tomo-angles. Instead, the fatty tissue volume may approximately be reconstructed with standard methods, such as shift-and-add methods, or iterative methods, and these values may be used as approximate estimates of fatty background for the thickness equalization. Alternatively, an approximate height map of the breast may be reconstructed in 3D, e.g. the mean of the different intersection lengths through a voxel, and these values may be used as an iso-contour estimate for the minimum filtration.

Furthermore, spectral imaging may also help to overcome the thickness-equalization problem in 2D mammographic imaging. A breast height map may be generated as described in WO2014097026A1 and then either used to derive the real iso-contour lines for the given minimum filtration method. Alternatively, the measured breast height values may be used to perform a peripheral equalization by adding homogenous attenuation, e.g. the attenuation of fatty tissue, according to distance difference between the compression paddles and the measured breast thickness for the given ray. In other words, the intersection length with air in the X-ray beam is virtually filled up with e.g. fatty tissue, leading to a homogenous image appearance.

Figure 4:
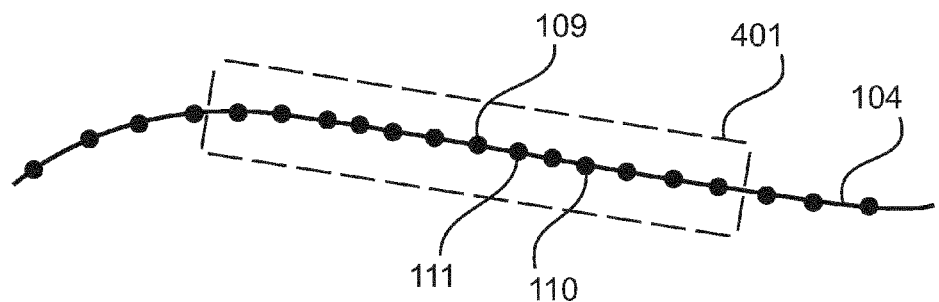
FIG. 4 shows an iso-contour along which pixel is arranged.

FIG. 4 shows an iso-contour 104 which intersects a plurality of pixel. During minimum filtering of the object data along the iso-contour 104 a first pixel 109 on the iso-contour is identified and its intensity value is determined. Also, the intensity values of neighboring, second pixel 110 are determined, and if one of these intensity values is lower than the intensity value of the first pixel 109, the value of the first pixel is replaced by this (minimum) intensity value, thus creating a minimum filtered image. The first pixel and the neighboring pixel, which are taken into account during this minimum filtering step, all lie on the iso-contour 104 and are located in virtual box 401, i.e. have not more than a maximum distance from first pixel 109.

After this minimum filtering step, box 401 is moved, in the (original) object data, one pixel further along the iso-contour 104, and the "new" first pixel is now pixel 111. The same procedure is now performed for pixel 111, which may result in a replacement of the value of pixel 111, in the minimum filtered image, by a lower pixel value of one of the neighboring pixel inside box 401 (which has been moved one pixel to the right). This method can be performed for each pixel on the iso-contour 104, after which a second iso-contour is determined, which is one pixel closer or further away from the skin line. The minimum filtering may stop after all pixels in the peripheral region of the object of interest have been "first pixel" during minimum filtering.

Figure 5:
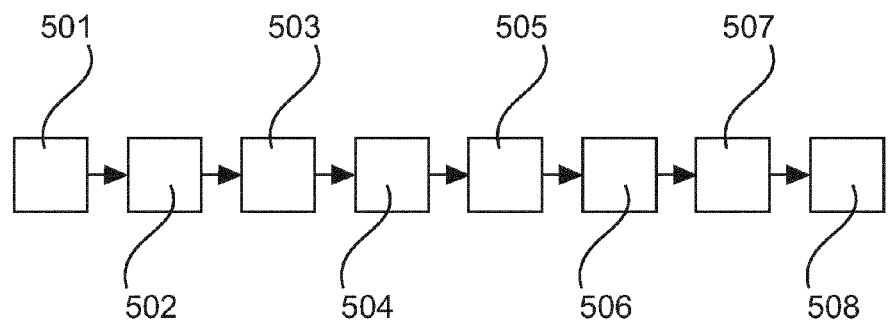
FIG. 5 shows a flow-chart of a method according to an exemplary embodiment of the invention.

FIG. 5 shows a flow-chart of a method according to an exemplary embodiment of the invention. In step 501, image data is acquired by the examination apparatus and stored in the storage unit in step 502. From the initial image data, a segmentation of the object data, i.e., the breast, and the non-object data is performed in step 503 by using an appropriate segmentation method. From the object data contour lines are derived that have the same distance to the breast skin line and/or which run along a line where the breast has a constant thickness (step 504). In step 505, the object data or image is pre-blurred with a small low-pass filter in order to get rid of noise peaks, as the minimum filtration is susceptible for negative noise spikes.

The output image is then generated by minimum filtering each image pixel in step 506, which involves looking up the minimum pixel values along the same iso-contour line for a given distance, e.g. 15 or 20 pixel in both directions. This results in an image which has less high-intensity pixel along the iso-contours of the breast and more background pixel. The image can then be treated with one or more peripheral equalization methods in step 507, to get an estimate of the breast thickness, which is then used for the final correction in step 508.

The minimum filtered image itself may not be suitable as a thickness estimate as its still could incorporate structures.

A low-pass filtering for the estimation of the mean level may still be required after the minimum filter.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE SIGNS 100 examination apparatus
101 storage unit
102 object of interest
103 processing unit
104 iso-contour
105 constant distance
106 peripheral edge (skin line)
107 object data
108 non-object data
109 first pixel
110 second pixel
111 pixel
121 compression plate
122 compression plate
123 X-ray source
124 central region
125 peripheral, non-compressed region
201 original image
202 image
203 image
204 diagram
205 plot
206 plot
207 plot
208 intersection
401 box
501 method step
502 method step
503 method step
504 method step
505 method step
506 method step
507 method step
508 method step

The invention claimed is:

1. An examination apparatus for examination of an object of interest, comprising:
a processor:
a storage readable by the processor and storing image data of an image of the object of interest, the image data comprising object data and non-object data; and
a non-transitory computer-readable medium storing instructions executable by the processor to perform a method including:
segmenting the object data from the non-object data;
determining a line, which is an iso-contour and extends at a constant distance from a boundary of the object of interest or which extends along a constant thickness of the object of interest;
generating a minimum filtered image by performing a minimum filtering of the object data along the iso-contour, thereby replacing a higher intensity value of a first pixel positioned on the iso-contour by a lower intensity value of a second pixel positioned on the iso-contour and in the neighborhood of the first pixel;
performing a peripheral equalization of the object data by:
determining a background data estimate by low-pass filtering the minimum-filtered image;
subtracting the background data estimate from the image data;
adding a desired homogenous background attenuation image to the image data.

2. The examination apparatus according to claim 1, wherein the method further includes, before the minimum filtering:
pre-blurring of the object data using a low-pass filter.

3. The examination apparatus according to claim 1, wherein the iso-contour is determined by evaluation of spectral data.

4. The examination apparatus according to claim 1, wherein the iso-contour is determined by identifying the boundary of the object of interest from the non-object data, the image data or the object data.

5. The examination apparatus according to claim 1, wherein the minimum filtering of the object data along the iso-contour comprises a selection of the first pixel, a determination of the intensity value of the first pixel, a determination of the intensity values of a predetermined number of pixel positioned on the iso-contour and adjacent to the first pixel, and a replacement of the intensity value of the first pixel by the lowest intensity value of the predetermined number of adjacent pixel.

6. The examination apparatus according to claim 1, wherein the peripheral equalization of the object data comprises a low-pass filtering.

7. The examination apparatus according to claim 1, wherein the examination apparatus is one of a two-dimensional mammography examination apparatus and a tomosynthesis examination apparatus.

8. A non-transitory computer readable medium storing instructions, which, when being executed by a processing unit, instruct the processing unit to:
access image data of an image of the object of interest, the image data comprising object data and non-object data;
segment the object data from the non-object data;
determine a line, which is an iso-contour and extends at a constant distance from a boundary of the object of interest or which extends along a constant thickness of the object of interest;

generate a minimum filtered image by performing a minimum filtering of the object data along the iso-contour, thereby replacing a higher intensity value of a first pixel positioned on the iso-contour by a lower intensity value of a second pixel positioned on the iso-contour and in the neighborhood of the first pixel; and perform a peripheral equalization of the object data by:
determining a background data estimate by low-pass filtering the minimum-filtered image;
subtracting the background data estimate from the image data; and
adding a desired homogenous background attenuation image to the image data.

9. The non-transitory computer readable medium according to claim 8, wherein the processing unit is adapted for performing, before the minimum filtering:
pre-blurring of the object data using a low-pass filter.

10. The non-transitory computer readable medium according to claim 8, wherein the iso-contour is determined by evaluation of spectral data.

11. The non-transitory computer readable medium according to claim 8, wherein the iso-contour is determined by identifying the boundary of the object of interest from the non-object data, the image data or the object data.

12. The non-transitory computer readable medium according to claim 8, wherein the minimum filtering of the object data along the iso-contour comprises a selection of the first pixel, a determination of the intensity value of the first pixel, a determination of the intensity values of a predetermined number of pixel positioned on the iso-contour and adjacent to the first pixel, and a replacement of the intensity value of the first pixel by the lowest intensity value of the predetermined number of adjacent pixel.

13. The non-transitory computer readable medium according to claim 8, wherein the peripheral equalization of the object data comprises a low-pass filtering.

14. A method of examining an object of interest, comprising:
acquiring image data of an image of the object of interest, the image data comprising object data and non-object data;
segmenting the object data from the non-object data;
determining a line, which is an iso-contour and extends at a constant distance from a boundary of the object of interest or which extends along a constant thickness of the object of interest;
generating a minimum filtered image by performing a minimum filtering of the object data along the iso-contour, thereby replacing a higher intensity value of a first pixel positioned on the iso-contour by a lower intensity value of a second pixel positioned on the iso-contour and in the neighborhood of the first pixel;
performing a peripheral equalization of the object data by:
determining a background data estimate by low-pass filtering the minimum-filtered image;
subtracting the background data estimate from the image data; adding a desired homogenous background attenuation image to the image data.

15. An examination apparatus for examination of an object of interest, the apparatus comprising:
a storage device configured to provide image data of an image of the object of interest, the image data comprising object data and non-object data;
at least one electronic processor programmed to:
segment the object data from the non-object data;
determine an iso-contour extending at a constant distance from a boundary of the object of interest or which extends along a constant thickness of the object of interest;
generate a minimum filtered image by replacing a higher intensity value of a first pixel positioned on the iso-contour by a lower intensity value of a second pixel positioned on the iso-contour and in the neighborhood of the first pixel;
perform a peripheral equalization of the object data by:
determining a background data estimate by low-pass filtering the minimum-filtered image;
subtracting the background data estimate from the image data;
adding a desired homogenous background attenuation image to the image data.

16. The examination apparatus according to claim 15, wherein the at least one electronic processor is further programmed to:
pre-blur of the object data using a low-pass filter before generating the minimum filtered image.

17. The examination apparatus according to claim 15, wherein the at least one electronic processor is further programmed to:
determine the iso-contour by evaluating spectral data of the object of interest.

18. The examination apparatus according to claim 15, wherein the at least one electronic processor is further programmed to:
determine the iso-contour by identifying the boundary of the object of interest from the non-object data, the image data or the object data.

19. The examination apparatus according to claim 15, wherein the minimum filtering includes:
selecting the first pixel;
determine an intensity value of the first pixel;
determine intensity values of a predetermined number of pixel positioned on the iso-contour and adjacent to the first pixel; and
replace the intensity value of the first pixel by the lowest intensity value of the predetermined number of adjacent pixel.

20. The examination apparatus according to claim 15, wherein the peripheral equalization of the object data comprises a low-pass filtering.

* * * * *